United States Patent [19]

Strickler et al.

[11] 3,931,327

[45] Jan. 6, 1976

[54] PROCESS FOR THE PREPARATION OF A DIKETONE DERIVATIVE

[75] Inventors: Hugo Strickler, Dardagny,Ge; Joseph J. Becker, Geneva; Gunther Ohloff, Bernex,Ge, all of Switzerland

[73] Assignee: Firmenich SA, Geneva, Switzerland

[22] Filed: Dec. 3, 1974

[21] Appl. No.: 529,229

[30] Foreign Application Priority Data
Dec. 7, 1973  Switzerland.................... 17173/73

[52] U.S. Cl............................ 260/586 P; 260/586 R
[51] Int. Cl.²........................................ C07C 45/00
[58] Field of Search..................... 260/586 R, 586 P

[56] References Cited
UNITED STATES PATENTS

| | | |
|---|---|---|
| 2,819,298 | 1/1958 | Isler et al........................ 260/586 P |
| 2,917,539 | 12/1959 | Isler et al........................ 260/586 P |
| 3,070,629 | 12/1962 | Ohloff et al..................... 260/586 P |
| 3,404,185 | 10/1968 | Thomas et al................... 260/586 P |

OTHER PUBLICATIONS

Ter–Sarkisyan et al., "Chem. Ab.," Vol. 68, 104589u, (1968).

Garbisch, "J.A.C.S.," Vol. 85, pp. 1696–1697, (1963).

*Primary Examiner*—Norman Morgenstern
*Attorney, Agent, or Firm*—Pennie & Edmonds

[57] ABSTRACT

Process for the preparation of a diketone derivative useful as perfuming and taste-modifying agent as well as intermediate for the preparation of compounds having utility in the pharmaceutical and dye-stuff industry.

9 Claims, No Drawings

PROCESS FOR THE PREPARATION OF A DIKETONE DERIVATIVE

SUMMARY OF THE INVENTION

This invention relates to the preparation of an alicyclic diketone having the formula

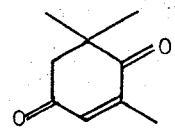

which compound is defined as being the 2,2,6-trimethylcyclohex-5-en-1,4-dione (hereinafter referred to as oxophorone).

More specifically, this invention relates to a process for the preparation of said diketone, which process comprises oxidizing, in the gas phase, 3,3,5-trimethyl-cyclohex-5-en-1-one in the presence of an oxygen containing derivative of vanadium by means of oxygen or an oxygen containing gas mixture.

BACKGROUND OF THE INVENTION 2,2,6-Trimethyl-cyclohex-5-en-1,4-dione and homologues thereof, are useful as starting materials in the synthesis of certain carotenoids (see e.g. O. Isler "Carotenoids" Birkhauser Verlag, Basel, 1971, page 130) and are also useful in the fields of flavouring and perfumery (see e.g. U.S. Pat. No. 3,380,456). Several methods are known for the synthesis of such compounds, usually starting from isophorone, i.e. 3,3,5-trimethyl-cyclohex-5-en-1-one, which is commercially available at a low price and in practically unlimited quantities. One such method, described in Tetrahedron Suppl., 8, 1–7 (1966), Helv.Chim.Acta, 39, 2041 (1956) and U.S. Pat. No. 2,917,539, is summarized in the following reaction scheme:

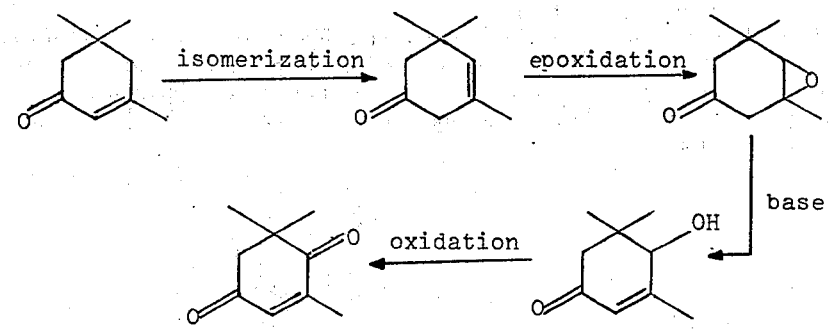

However, this synthetic route suffers from the disadvantages of producing low yields of the desired diketone, of comprising several successive reaction steps, and of requiring the use of relatively expensive reagents, so that it is unsuitable for use on an industrial scale.

In order to provide an industrially more advantageous synthetic route, we have attempted to prepare 2,2,6-trimethyl-cyclohex-5-en-1,4-dione by oxidizing 4-bromo-3,3,5-trimethyl-cyclohex-2-en-1-one with nitropropane or with a tertiary amine oxide such as trimethylamine oxide. However, instead of the desired diketone, this reaction yielded, 2,4,4-trimethyl-cyclohex-5-en-6-ol-1-one, i.e. the compound of formula

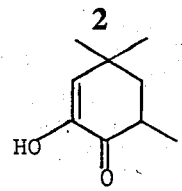

(see German Offenlegungschrift No. 2,202,066).

The known method for the direct oxidation of an allylic methylene group to give the corresponding carbonyl derivative, by means of actinic irradiation in an aqueous medium in the presence of N-bromosuccinimide (see e.g. Chem. Comm., 1969, 1220), proved unsuccessful when applied to isophorone. Other known oxidation methods were also unsuccessful, including those described in J. Am. Chem. Soc. 79, 6308 (1957), J.Am.Chem.Soc. 83, 2952, (1961), J. Org. Chem. 33, 3566, (1968), Tetrahedron Letters 1972, 1823, and Liebigs Ann.Chem. 627, 237, (1959): all of these methods either did not produce any appreciable amount of the desired ketone, or gave yields too poor for practical utility.

PREFERRED EMBODIMENTS OF THE INVENTION

It has now surprisingly been found that good yields of oxophorone can be obtained by direct oxidation, in the gas phase, of isophorone by means of oxygen or an oxygen containing gas mixture, in the presence of an oxygen containing derivative of vanadium.

The oxidation is performed by pure oxygen or by a mixture comprising oxygen together with an inert gas, e.g. nitrogen, helium or argon. For all practical purposes however, air or an oxygen enriched air, more preferentially a nitrogen-oxygen mixture containing 20 to 95 percent (v/v) oxygen, are used. The best results were achieved by using an oxygen enriched air whose oxygen content is of about 90 percent (v/v).

The oxidation can be carried out at barometric pressure and at a temperature of from about 180° to 400°C. The lower limit indicated above depends on the volatility of starting isophorone at normal conditions. Therefore, whenever the oxidation is effected at a pressure lower than the barometric pressure, this value may be decreased proportionally.

It has been observed that whenever pure oxygen was used as oxidizing gas it was convenient to operate at a temperature lying in the vicinity of the above given lower limit. On the contrary, when mixtures comprising oxygen and nitrogen were used, suitable reaction temperatures were of from about 180° to 400°C, preferably of from 200° to 250°C, more preferably of 220°–240°C. At temperature higher than 400°C, the main oxidation product was accompanied by a certain amount of by-products of different and unidentified nature.

The oxidation is effected in the presence of an oxygen containing derivative of vanadium. Though, vanadium pentoxide was used as base material for the preparation of the said catalyst, it could not be established with certainty whether such an oxide did not undergo some preliminary transformations in the course of its manufacture. It is not unreasonable in fact to assume that the acting oxidation catalyst is constituted by a mixture of vanadium$^{IV}$, vanadium$_V$ and vanadium$^{VI}$ oxides ($V_2O_4$, $V_2O_5$ and $VO_3$), wherein $V_2O_5$ is the main component. Owing to this uncertainty, in so far as structure is concerned, the content of vanadium oxide will be here expressed in percent by weight of $V_2O_5$ based on the total weight of the oxidation catalyst. The content thus defined represents the proportion of $V_2O_5$ initially employed for the catalyst manufacture. Typically, suitable catalysts comprise of from about 5 to 25 percent of vanadium oxide. A catalyst containing about 15 percent of vanadium oxide is preferred.

The oxidation catalysts are used on an inert mineral support, such as e.g. porous silica. This latter can be under the form of powdery pumice-stone or of diatomaceous earth, e.g.. The best results were achieved by preliminary impregnating said solid support with an alcali metal phosphate. Lithium phosphate ($Li_3PO_4$) was preferred. It was employed at a concentration of from about 0.1 to 3 percent, preferably at about 1 percent by weight based on the total weight of the chosen support.

According to a preferred embodiment of the process of this invention, the catalyst is preliminarily subjected to an activation by heating it under a stream of air or, preferably, oxygen. Such an operation is performed at a temperature of from about 200° to 400°C, preferably at about 350°C.

In accordance with another preferred embodiment of the invention, the oxidation of isophorone is effected by means of a 90 percent (v/v) oxygen containing mixture of nitrogen and oxygen, at barometric pressure and at a temperature of from 220° to 240°C in the presence of vanadium pentoxide deposited at about 15 percent by weight on porous silica preliminarily impregnated with 1 percent lithium phosphate.

The following compounds were thus isolated at the end of the reaction:

4% of β-phorone and γ-phorone

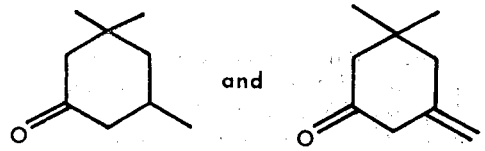

39% starting isophorone

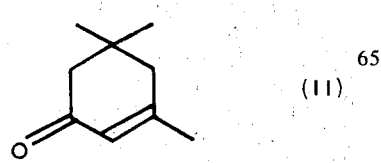

(II)

29% oxophorone

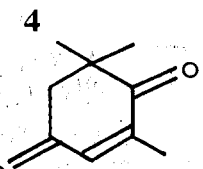

(I)

26% 5,5-dimethyl-3-formyl-cyclohex-2-en-1-one

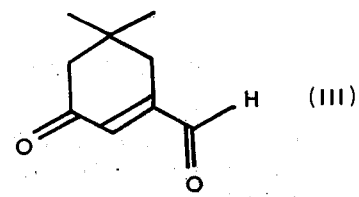

(III)

Each of the above compounds can be isolated from the others by means of conventional techniques, e.g. by fractional distillation by means of highly efficient separating columns or by vapour phase chromatography.

Compound (III) is a new compound and owing to its structure it represents a useful intermediate for the preparation of compounds interesting for the perfumery and the flavour industry.

The process of this invention provides a simple and economical route to oxophorone by making use, as starting materials and reagents, of readily available cheap compounds. The apparatus employed for carrying out the said process is rather simple and consists in a steel column of various lengths and sections. Said column is filled with the chosen catalyst and set to a preselected temperature by means of an external thermostatic heating device. Once the desired reaction conditions are reached, vapours of isophorone are let through the column by introducing them at one of its ends, either continuously or intermittently, together with the oxidizing gas mixture. This latter can be preliminarily heated at the required temperature before introduction.

It is likely that the oxidation reaction which characterizes the process of the present invention can be applied also to the oxidation of alkyl substituted derivatives of isophorone of formula

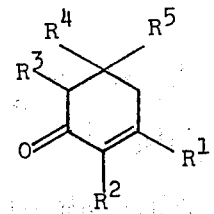

and homologue of 2,2,6-trimethyl-cyclohex-5-en-1-one of formula

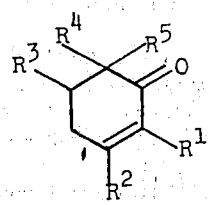

wherein one of symbols $R^1$, $R^2$ and $R^3$ represents an alkyl radical or a hydrogen atom, and the others hydrogen or alkyl radicals, respectively, and wherein each of symbols $R^4$ and $R^5$ represent a lower alkyl, to give the corresponding dioxo derivatives.

The following example illustrates the invention in a more detailed manner; the temperatures are given in degrees centigrade and the abbreviations have the meaning common in the art.

EXAMPLE

A Catalyst manufacture

A clear solution was prepared by dissolving 100 g of $V_2O_5$ in 4 l of warm 30 percent aqueous solution of ammonia, whereupon there were added 570 g of powdery pumice-stone (average section: 2–3 mm) preliminarily impregnated with lithium phosphate ($Li_3PO_4$) at a concentration of 1 percent by weight based on the total weight of the treated pumice-stone. The mass thus obtained was finally dried by evaporation under reduced pressure: 40°–50°/15 Torr. The yellow powdery mass resulting from the above treatment was then introduced into a stainless steel column of 2 m length and 18 mm section and heated therein as follows:
24 h at 250°
24 h at 300° and
24 h at 350°.

While heating, a stream of air at a constant flow of 4 l /h cm² was passed through the column.

B. Isophorone oxidation

The column filled with the above prepared catalyst was set in a thermostatic oven and kept therein at 230°, while a stream of oxygen enriched air (90:10 v/v) preheated at 80° was passed through the column. The gas flow was 20 l /h cm² . 3 g of isophorone were then let into one end of the column by successively injecting 0.5 g aliquotes every ten minutes. The reaction mixture was collected in a cooled trap (0°) at the other end of column. A vpc analysis (CARBOWAX 20 M column; 3 m; 160°) indicated that said mixture comprised:
a. ca. 4 percent of a mixture of β- and γ-phorone;
b. 39 percent of isophorone;
c. 29 percent of oxophorone (A);
d. 26 percent of 5,5-dimethyl-3-formyl-cyclohex-2-en-1-one (B), and
e. ca. 3 percent of unidentified products.

Compounds A and B were isolated in their pure form from the obtained mixture by means of preparative vpc and showed the following analytical data:

A. B.p. 95°–6°/12 Torr; $n^{20}_D = 1.4880$

The IR and NMR spectra were identical to those of a pure sample prepared in accordance with Helv.Chim. Acta 39, 2041 (1956)

B. $d^{20}_4 = 1.044$; $n^{20}_D = 1.4944$ IR: 3330, 2940, 1765, 1690, 1110, 908 cm$^{-1}$; NMR: 1.08 (6H, s), 2.34 (4H, d, J = 2Hz); 6.46 (1H, t, J = 2Hz); 9.70 (1H, s) δ ppm; MS: $M^+ = 152$; m/e: 137, 124, 109, 96, 81, 68, 53.

What is claimed is:

1. Process for the preparation of 2,2,6-trimethyl-cyclohex-5-en-1,4-dione, which comprises oxidizing, in the gas phase, 3,3,5-trimethyl-cyclohex-5-en-1-one in the presence of vanadium oxide or a mixture of vanadium oxides deposited on an inert solid support by means of oxygen or an oxygen containing gas mixture.

2. Process according to claim 1, wherein the oxidation is performed by means of an oxygen containing gas mixture comprising of from about 20 to 95 percent by volume of oxygen.

3. Process according to claim 2, wherein the oxygen containing gas mixture comprises about 90 percent by volume of oxygen.

4. Process according to claim 1, wherein the oxidation is effected at barometric pressure and at a temperature of from about 180° to 400°C.

5. Process according to claim 4, wherein the oxidation is effected at a temperature of from about 200° to 250°C.

6. Process according to claim 1, wherein the inert solid support is porous silica preliminary impregnated with a mineral base.

7. Process according to claim 1, wherein the oxidation is performed in the presence of vanadium oxide, or a mixture of vanadium oxides, deposited at a concentration of from about 5 to 25 percent by weight of $V_2O_5$ on porous silica containing of from about 0.1 to 3 percent by weight of an alkali metal phosphate.

8. Process according to claim 7, wherein the concentration of vanadium oxide, or mixture of vanadium oxides, is of about 15 percent by weight of $V_2O_5$ deposited on porous silica containing about 1 percent by weight of lithium phosphate.

9. Process according to claim 1, wherein the vanadium oxide catalyst is preliminarily activated by heating under a stream of air at a temperature of from about 200° to 400°C.

* * * * *

UNITED STATES PATENT AND TRADEMARK OFFICE
CERTIFICATE OF CORRECTION

PATENT NO. : 3,931,327
DATED : January 6, 1976
INVENTOR(S) : Hugo Strickler, Joseph J. Becker and Gunther Ohloff It is certified that error appears in the above-identified patent and that said Letters Patent are hereby corrected as shown below:

Column 3, line 11, "vanadium$_V$" should be --vanadium$^V$--.

Column 5, line 10, "A Catalyst manufacture" should be
--A) Catalyst manufacture--

Column 5, line 30, "B. Isophorone oxidation" should be
--B) Isophorone oxidation--

Signed and Sealed this eighth Day of June 1976

[SEAL]

Attest:

RUTH C. MASON
*Attesting Officer*

C. MARSHALL DANN
*Commissioner of Patents and Trademarks*